United States Patent [19]

Williams, III et al.

[11] 4,257,953

[45] Mar. 24, 1981

[54] METHOD FOR MAKING BISPHENOXIDE SALTS AND BISIMIDES DERIVED THEREFROM

[75] Inventors: Frank J. Williams, III, Scotia; Brent A. Dellacoletta, Clifton Park, both of N.Y.

[73] Assignee: General Electric Company, Schenectady, N.Y.

[21] Appl. No.: 37,442

[22] Filed: May 9, 1979

[51] Int. Cl.³ .......................................... C07D 209/48
[52] U.S. Cl. ............................ 260/326 R; 260/326 A; 260/326 HL; 260/326 N; 260/326 S; 568/723; 568/724
[58] Field of Search ........... 260/326 R, 326 S, 326 A, 260/326 N, 326 HL; 568/723, 724

[56] References Cited

U.S. PATENT DOCUMENTS

| | | | |
|---|---|---|---|
| 3,852,242 | 12/1974 | White | 568/723 |
| 3,957,862 | 5/1976 | Heath et al. | 562/468 |
| 4,048,190 | 9/1977 | Johnson et al. | 260/326 N |

OTHER PUBLICATIONS

C. Stark, J. Amer. Chemical Soc., 93:1 (1971), Phase Transfer Catalysis, I. Heterogeneous Reactions Involving Anion Transfer by Quaternary Ammonium and Phosphonium Salts.

*Primary Examiner*—Donald G. Daus
*Assistant Examiner*—M. C. Eakin
*Attorney, Agent, or Firm*—William A. Teoli; James C. Davis, Jr.

[57] ABSTRACT

A method is provided for making alkali metal bisphenoxide salts by refluxing a heterogenous mixture of a non-polar organic solvent and an aqueous solution of an alkali metal bisphenoxide. These bisphenoxide salts can be used thereafter to make aromatic bis(ether phthalimides) by reaction with nuclear ring substituted N-organo phthalimides.

5 Claims, No Drawings

METHOD FOR MAKING BISPHENOXIDE SALTS AND BISIMIDES DERIVED THEREFROM

CROSS REFERENCE TO RELATED APPLICATIONS

Reference is made to copending applications Ser. No. 037,441, filed May 9, 1979 of Frank J. Williams, III, for Method of Making Ether Phthalimide and Ser. No. 037,440, filed May 9, 1979, now U.S. Pat. No. 4,202,993, of Tohru Takekoshi for Method for Making Substantially Anhydrous Alkali Metal Bisphenol Salts, filed concurrently herewith and assigned to the same assignee as the present invention.

BACKGROUND OF THE INVENTION

The present invention relates to a method for making alkali metal phenoxide salts. More particularly, the present invention relates to a method for making aromatic ether imides based on the use of an alkali metal phenoxide salt obtained by azeotroping a water-hydrocarbon solvent mixture from an aqueous mixture of an in situ formed alkali metal phenoxide salt.

Prior to the present invention, as shown by Wirth et al U.S. Pat. No. 3,787,364, assigned to the same assignee as the present invention, alkali metal phenoxide salts were made by effecting reaction between alkali metal hydroxides and bisphenols in the presence of water, where the water was removed by azeotropic distillation using a hydrocarbon solvent and a dipolar aprotic solvent. Although this procedure was effective for making polyetherimides, it could not be used without the presence of the dipolar aprotic solvent which rendered the procedure economically less attractive. Improved results were achieved when the bisphenoxide salt was made in accordance with the procedure of White U.S. Pat. No. 3,852,242, assigned to the same assignee as the present invention, based on the use of an alkali metal alkoxide which was reacted with a bisphenol to produce the alkali metal bisphenoxide in the absence of water. An additional procedure is shown by copending application of Tohru Takekoshi, Ser. No. 374,440, now U.S. Pat. No. 4,200,993, based on the rapid separation of water, such as by flashing from a hydrated alkali metal bisphenoxide, or an aqueous slurry containing stoichiometric amounts of alkali metal hydroxide and the bisphenol. The advantages of the procedure of Takekoshi is that elevated temperatures can be used, for example, above 100° C. and as high as 300° C. to effect the rapid separation of water from aqueous bisphenoxide alkali metal hydroxide slurry, or the hydrate of the alkali metal bisphenoxide salt to produce a substantially anhydrous bisphenoxide salt. Although the procedure of Takekoshi also in effective for making substantially anhydrous alkali metal bisphenoxides, special equipment, such as spray dryers, drum dryers, etc., are needed to render the procedure economically feasible.

The present invention is based on the discovery that unlike the procedures of the prior art requiring either expensive dipolar aprotic solvents, special equipment or the synthesis of alkali metal alkoxides, substantially anhydrous alkali metal bisphenoxides can be made by initially preparing a homogeneous solution of an aqueous metal hydroxide and a bisphenol and thereafter combining the aforementioned aqueous bisphenoxide solution with a substantially inert hydrocarbon solvent to produce a heterogenous mixture which is thereafter refluxed to effect the separation of water by azeotropic distillation. The surprising feature of the present invention is that unless the initial mixture of alkali metal hydroxide and bisphenol is in the form of a homogeneous solution, effective removal of water cannot be achieved and the resulting alkali metal bisphenoxide salt does not provide for satisfactory yields of aromatic ether imide when used in reaction with substituted phthalimides, such as nitro phthalimide.

STATEMENT OF THE INVENTION

There is provided by the present invention, a method for making an anhydrous alkali metal phenoxide salt of the formula,

$$R^1 \text{-}(OM)_a, \quad (1)$$

which comprises refluxing and agitating a heterogeneous mixture of a nonpolar organic solvent having a boiling point in the range of 80° C. to 200° C. at 760 torr and an aqueous solution of a phenol of the formula,

$$R^1 \text{-}(OH)_a, \quad (2)$$

and substantially stoichiometric equivalents of such phenol and an alkali metal hydroxide to effect the separation of water in the form of an azeotrope from the resulting mixture until it is substantially anhydrous, where $R^1$ is a $C_{(6-30)}$ aromatic organic radical, M is an alkali metal ion, a is an integer equal to 1 or 2, and when a is 1, $R^1$ is monovalent and when a is 2, $R^1$ is divalent.

Another aspect of the present invention is directed to a method for making aromatic ether imides of the formula,

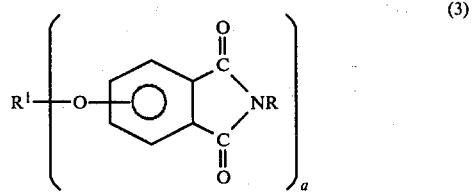

utilizing an effective amount of a phase transfer catalyst of the formula,

$$(R^2)_4QY, \quad (4)$$

where $R^1$ and a are as previously defined, R is a monovalent radical selected from hydrogen, a $C_{(1-8)}$ alkyl radical and a $C_{(6-13)}$ aryl radical, $R^2$ is a $C_{(1-16)}$ alkyl radical and a $C_{(6-13)}$ aromatic radical, Q is a group Va element selected from N and P, and Y is a halogen or carbethoxy radical.

The present invention also relates to an improvement over the method of copending application RD-10770 since the introduction of a preformed bisphenoxide necessitates special safeguards to minimize introduction of moisture and oxygen into the system which can result in reduced yields. Accordingly, in the method of making aromatic ether imides of formula (3) by heating a substituted phthalimide of the formula,

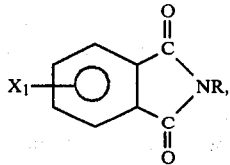

where R is as previously defined and $X_1$ is a radical selected from nitro and halo and an alkali metal phenoxide salt of formula (1) in the presence of a nonpolar organic solvent and an effective amount of a phase transfer catalyst whereby special procedures can be required to minimize the introduction of moisture and oxygen into the reaction mixture, the improvement which comprises utilizing as the alkali metal phenoxide salt in the aromatic ether imide reaction mixture, the product obtained by refluxing a heterogenous mixture of a hydrocarbon solvent having a boiling point in the range of 80° C. to 200° C. at 760 torr and an aqueous solution of substantially equal moles of a phenol of formula (2) and an alkali metal hydroxide to effect the separation of water from the heterogenous mixture by azeotropic distillation until the resulting mixture is substantially anhydrous.

Radicals included by R, are for example, phenyl, tolyl, xylyl, naphthyl, chlorophenyl, bromonaphthyl, etc., and alkyl radicals such as methyl, ethyl, propyl, etc. Radicals included by $R^1$ are the aforementioned monovalent aromatic radicals included by R, divalent aromatic radicals, such as phenylene, tolylene, naphthylene, etc., $R^1$ more particularly includes

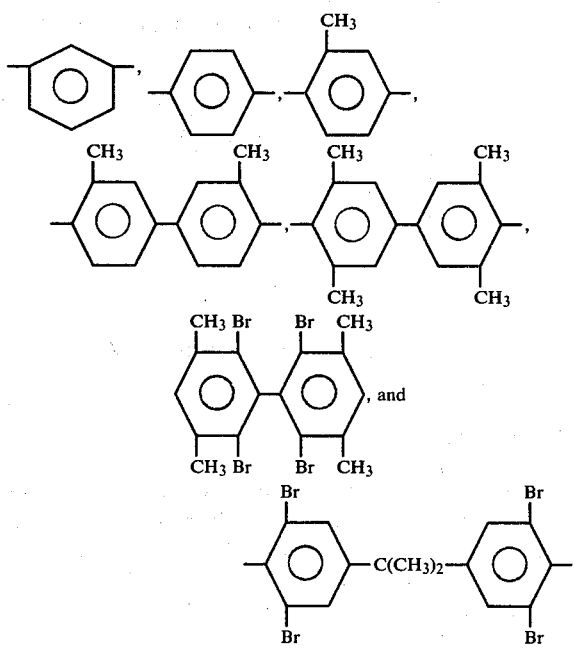

and divalent organic radicals of the general formula,

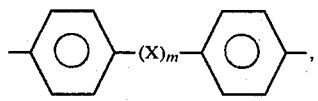

where X is a member selected from the class consisting of divalent radicals of the formula,

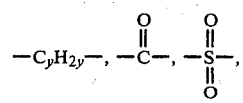

—O—, and —S—, where m is 0 or 1, and y is a whole number from 1 to 5.

Radicals included by $R^2$ are, for example, propyl, butyl, pentyl, hexyl, heptyl, octyl and phenyl. M is more particularly sodium, potassium, lithium, rubidium, etc; Y is more particularly, chloro, bromo, iodo, acetato, etc.

Some of the alkali salts of the above-described alkali phenoxide of formula (1) are sodium and potassium salts phenols, such as phenol, cresol, naphthol, etc.; dihydric phenols, for example,
2,2-bis(2-hydroxyphenyl)propane;
2,4'-dihydroxydiphenylmethane;
bis(2-hydroxyphenyl)methane;
2,2-bis-(4-hydroxyphenyl)propane hereinafter identified as "bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4'-dihydroxydiphenylmethane;
4,4'-dihydroxybenzophenone;
and 4,4'-dihydroxydiphenylether.

Included by the substituted phthalimides of formula (5), are for example, 4-nitro,N-phenylphthalimide; 3,-nitro,N-phenylphthalimide; 4-nitro,N-methylphthalimide; 3-nitro,N-methylphthalimide; 4-fluoro,N-methylphthalimide; 3-flouro,N-methylphthalimide; 4-chloro,N-methylphthalimide; 3-chloro,N-methylphthalimide, etc. These substituted phthalimides can be made by standard procedures, such as effecting reaction between substantially equal moles of the corresponding phthalic anhydride and an organic amine in the presence of refluxing acetic acid. Included by the organic amines which can be used, are for example, aniline, toluidene, etc., methylamine, ethylamine, etc. Included by the phase transfer catalysts of formula (4), are for example, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride, Aliquat 336 phase transfer catalyst (methyltrioctylammonium chloride, manufactured by the General Mills Company), tetrabutylphosphonium bromide, tetraphenylphosphonium bromide, tetraphenylammonium bromide, tetrabutylphosphonium chloride, etc.

In the practice of the invention, a heterogenous mixture of an aqueous solution of alkali metal bisphenoxide salt and a nonpolar organic solvent having a boiling point of from 80° C. to 200° C. at 760 torr, is refluxed until the refluxing nonpolar organic solvent can be recovered substantially free of water. Those skilled in the art know that nonpolar organic solvents, such as toluene, can dissolve up to about 0.01% by weight water without effecting its clarity. Small amounts of residual water can therefore be readily detected. In forming the heterogenous mixture, the order of addition of the nonpolar organic solvent and the aqueous solution of the alkali metal phenoxide salt is not critical. There is preferably used substantially stoichiometric equivalents of alkali metal hydroxide and bisphenol in forming the alkali metal phenoxide salt; however, up to a 5% stoichiometric excess of alkali metal hydroxide can be tolerated without substantially adverse results.

Nonpolar organic solvents which can be employed in the practice of the method of the present invention are, for example, toluene, xylene, chlorobenzene, benzene, etc.

In preparing the aromatic bis(ether phthalimide), the reaction can best be run using a solids concentration, i.e., $$\frac{\text{weight of reaction solids}}{\text{volume of nonpolar organic solvent}} \times 100,$$

having a value of about 5% to 150% and preferably from 85-95%. Preferably, equivalent amounts of the bisphenoxide salt and substituted phthalimide can be used, while higher or lower amounts of the reactant will not substantially interfere with the formation of the desired ether phthalimide. In preparing the aromatic bis(ether phthalimide), there is preferably used about 2 mols of the substituted phthalimide, per mol of the bisphenoxide salt. The phase transfer catalyst as previously defined can be utilized at from 0.0005 equivalent to 2 equivalents of the catalyst, per equivalent of alkali bisphenoxide and preferably from 0.20 to 0.05 equivalent.

The ether phthalimide can be recovered from the reaction mixture by a variety of procedures. One procedure, for example, is allowing the reaction mixture to cool to effect separation followed by recovery of the ether phthalimide by filtration. Preferably, however, because of the partial solubility of the ether phthalimide in various nonpolar organic solvents, precipitation of the ether phthalimide can be facilitated by use of a precipitating solvent, for example, methanol, followed again by a standard recovery technique, such as filtration, centrifuging, decantation, etc. Alternatively, the ether phthalimide can be extracted from the reaction mixture with a solvent such as methylene chloride, chloroform, etc., washed with water to effect removal of the inorganic salts, and recovered by the removal of the organic solvent under reduced pressure.

The following examples are given by way of illustration and not by way of limitation. All parts are by weight and all mixtures are agitated, for example, stirred during reflux.

EXAMPLE 1

A mixture of 364.8 parts of bisphenol-A, 254 parts of a 50.5% aqueous sodium hydroxide solution and 615 parts of water was refluxed under nitrogen for 0.5 hour to give a homogenous solution. The mixture was cooled to 85° C. and about 1,030 parts of toluene was added. The mixture was heated at reflux for 4 hours and water was removed by azeotropic distillation. At this point, the inside wall of the reaction vessel was scraped to remove caked product. An additional 1,030 parts of toluene was then added to the mixture with vigorous stirring and the mixture was azeotropically dried for 2 hours. About 1000 parts of toluene was removed by distillation and 12.9 parts of tetrabutylammonium bromide and 659 parts of 4-nitro-N-methylphthalimide were added. The mixture was heated at reflux for 0.5 hour, cooled to around 70° C. and the mixture was diluted with about 1950 parts of methanol. A product precipitated from the mixture which was recovered by filtration which was thoroughly washed with additional methanol and dried to give 313.6 parts of product (a 93% yield). Based on method of preparation, the product was 2,2-bis[4-(N-methylphthalimide-4-oxy)phenyl]propane.

The above ether imide was found to have a color number of 2.9 as measured on a Carey Model 14 Spectrophotometer. A typical color number of the same aromatic bis(ether imide) was found to be 150-160 when prepared by a procedure employing a dipolar aprotic solvent in combination with an alkali metal hydroxide.

The same procedure was repeated to prepare the aromatic bis(ether phthalimide) except in preparing the bisphenoxide salt no additional water was added to the 50% aqueous sodium hydroxide solution. When the resulting mixture was heated to reflux, a homogenous solution was not obtained. There was obtained only a 5% yield of the desired bisetherimide.

EXAMPLE 2

Example 1 was repeated, except that 4-fluoro-N-methylphthalimide was used instead of 4-nitro-N-methylphthalimide. There was obtained an 89% yield of a pure aromatic bis(ether phthalimide) which was identical to the bisimide of Example 1.

EXAMPLE 3

A mixture of 20 parts of 4,4'-dihydroxydiphenyl sulfide, 14.5 parts of 50.6% sodium hydroxide and 36 parts of water was refluxed for 10 minutes to produce a homogenous solution. There was added to the solution about 86 parts of toluene and the mixture was dried as in Example 1 by effecting the removal of water by azeotropic distillation. There was then added to the mixture 37.7 parts of 4-nitro-N-methylphthalimide and 2.95 parts of tetrabutylammonium bromide. The mixture was then refluxed for 1 hour. Following the procedure of Example 1, there was obtained 13.8 parts or a 28% yield of a bis(ether imide) having the formula,

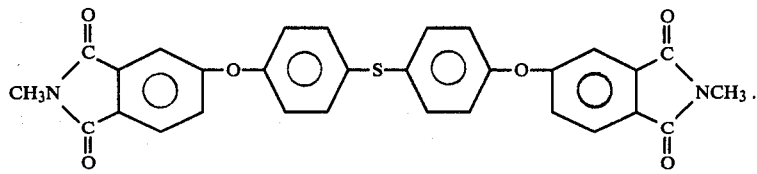

The identity of the bisimide was confirmed from its $^{13}C$ NMR analysis and from a comparison to an authentic sample.

EXAMPLE 4

A mixture of 21.93 parts of 4,4'-dihydroxydiphenyl-sulfone, 13.9 parts of 50.6% aqueous sodium hydroxide and 17 parts of water was refluxed for 14 minutes. To the resulting solution, there was added about 86 parts of toluene and the mixture was refluxed and the water was removed from the mixture by azeotropic distillation. About 17 parts of toluene was then distilled from the mixture and there was added 2.84 parts of tetrabutylammonium bromide and 36.1 parts of 4-nitro-N-methylphthalimide. The solution was heated at reflux for 16 hours. Following the procedure of Example 1, there was obtained 38.3 parts or a 77% yield of product. Based on method of preparation and $^{13}C$ NMR the product was

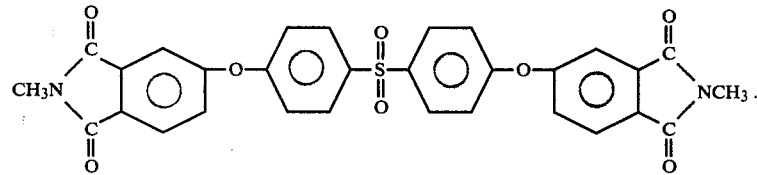

EXAMPLE 5

A mixture of 20 parts of bisphenol-A, 13.9 parts of a 50% aqueous sodium hydroxide solution and 34 parts of water was heated at reflux for 30 minutes. There was added about 87 parts of toluene to the resulting solution and the mixture was then refluxed and water azeotropically distilled in accordance with the procedure of Example 1. After about 71 parts of toluene had been removed from the mixture, there was added 2.2 parts of Aliquat 336, which had been azeotropicaly dried in toluene and 36.1 parts of 4-nitro-N-methylphthalimide, the mixture is refluxed from 1 hour. Following the procedure of Example (1), there was obtained 44.8 parts of bisimide (93.5% yield).

EXAMPLE 6

The above procedure was repeated except that an aqueous potassium hydroxide solution was used in place of the aqueous sodium hydroxide solution. Following the same recovery procedure, there was obtained 36% yield of the aromatic bis(ether phthalimide).

Although the above examples are directed to only a few of the very many variables within the scope of the method of the present invention, it should be understood that a much broader variety of aromatic bis(ether phthalimide)s can be made in accordance with the procedures utilizing the materials set forth in the disclosure preceding these examples.

What we claim as new and desire to secure by Letters Patent of the United States is:

1. In the method of making aromatic either imides of the formula,

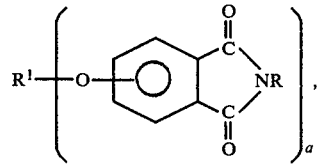

by heating a substituted phthalimide of the formula,

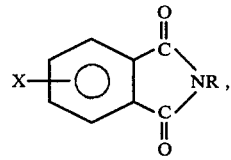

and a preformed alkali metal phenoxide salt of the formula,

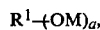

in the presence of a nonpolar organic solvent and an effective amount of a phase transfer catalyst, whereby special procedures are required to minimize the introduction of moisture and oxygen into the reaction mixture, the improvement which consists essentially of utilizing as the alkali metal phenoxide salt in the aromatic ether imide reaction mixture, the product obtained by refluxing a heterogenous mixture of a hydrocarbon solvent having a boiling point in the range of 80° C. to 200° C. at 760 torr and an aqueous solution of substantially equal moles of a phenol of the formula,

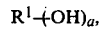

and alkali metal hydroxide to effect the separation of water from the heterogenous mixture by azeotropic distillation until the resulting mixture is substantially anhydrous, where R is a monovalent group selected from hydrogen, a $C_{(1-8)}$ alkyl group and a $C_{(6-13)}$ aryl group, $X_1$ is a member selected from the group consisting of nitro and halo, $R^1$ is an aromatic group selected from the group consisting of a $C_{(6-30)}$ aromatic carbocyclic group, a halogenated $C_{(6-30)}$ aromatic carbocyclic group and an alkylated $C_{(6-30)}$ aromatic carbocyclic group and a divalent organic group of the formula,

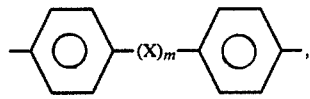

where X is a member selected from the group consisting of divalent groups of the formula,

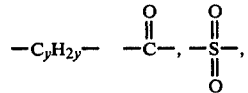

—O—, and —S—, m is 0 or 1, y is a whole number from 1 to 5 and a is an integer equal to 1 or 2, and when a is 1, $R^1$ is monovalent and when a is 2, $R^1$ is divalent.

2. A method in accordance with claim 1, where the alkali metal phenoxide salt is the disodium salt of bisphenol-A.

3. A method in accordance with claim 1, where the substituted phthalimide is 4-nitro-N-methylphthalimide.

4. A method in accordance with claim 1, where the phase transfer catalyst is tetrabutylammonium bromide.

5. A method in accordance with claim 1, where the hydrocarbon solvent is toluene.

* * * * *